US008716260B2

(12) United States Patent
Lautt et al.

(10) Patent No.: US 8,716,260 B2
(45) Date of Patent: May 6, 2014

(54) USE OF S-ADENOSYLMETHIONINE, VITAMIN E, AND VITAMIN C FOR THE TREATMENT OF OXIDATIVE LIVER INJURY

(75) Inventors: Wilfred Wayne Lautt, Winnipeg (CA); Zhi Ming, Winnipeg (CA)

(73) Assignee: University of Manitoba, Winnipeg, Manitoba (CA)

( * ) Notice: Subject to any disclaimer, the term of this patent is extended or adjusted under 35 U.S.C. 154(b) by 312 days.

(21) Appl. No.: 13/117,692

(22) Filed: May 27, 2011

(65) Prior Publication Data

US 2011/0230434 A1 Sep. 22, 2011

Related U.S. Application Data

(62) Division of application No. 11/814,866, filed as application No. PCT/CA2006/000108 on Jan. 26, 2006, now Pat. No. 8,063,024.

(60) Provisional application No. 60/646,594, filed on Jan. 26, 2005.

(51) Int. Cl.
*A61K 31/70* (2006.01)
*A61K 31/355* (2006.01)
*A61K 31/34* (2006.01)

(52) U.S. Cl.
USPC ............................. 514/46; 514/458; 514/474

(58) Field of Classification Search
USPC ........................................... 514/46, 458, 474
See application file for complete search history.

(56) References Cited

U.S. PATENT DOCUMENTS

| | | | |
|---|---|---|---|
| 3,893,999 | A | 7/1975 | Fiecchi |
| 4,057,686 | A | 11/1977 | Fiecchi |
| 5,078,989 | A | 1/1992 | Ando et al. |
| 5,137,723 | A | 8/1992 | Yamamoto et al. |
| 6,596,701 | B1 | 7/2003 | Schwartz et al. |
| 2004/0220118 | A1 | 11/2004 | Bland et al. |
| 2004/0254095 | A1 | 12/2004 | Martin et al. |

FOREIGN PATENT DOCUMENTS

WO    WO 02/092105 A1    11/2002

OTHER PUBLICATIONS

Matsuki et al., "Effects of Ascorbic Acid on Iproniazid-Induced Hepatitis in Phenobarbital-Treated Rats", Biological and Pharmaceutical Bulletin, vol. 17, No. 8, pp. 1078-1082 (1999).*
Baron et al., 1999, "Role of glutathione, lipid peroxidation and antioxidants on acute bile-duct obstruction in the rat." *Biochimica et Biophysica Acta* 1472: 173-180.
Bates et al., 1997, "Antioxidant status and lipid peroxidation in diabetic pregnancy." *British Journal of Nutrition* 78: 523-532.
Bruck et al., 2001, "Prevention of hepatic cirrhosis in rats by hydroxyl radical scavengers." *Journal of Hepatology* 35: 457-464.

Bruck et al., 2004, "Melatonin inhibits nuclear facot kappa B activation and oxidative stress and protects against thioacetamide induced liver damage in rats." *Journal of Hepatology* 40: 86-93.
Ceriello, 1999, "Hyperglycaemia: the bridge between non-enzymatic glycation and oxidative stress in the pathogenesis of diabetic complications." *Diab. Nutr. Metab.* 12: 42-46.
Deulofeu et al., 2000, "S-adenosylmethionine prevents hepatic tocopherol depletion in carbon tetrachloride-injured rats," *Clin. Sci.* 99: 315-320.
Evans et al., 1997, "Antioxidant properties of S-adenosyl-L-methionine: a proposed addition to organ storage fluids." *Free Radic Biol Med* 23(7): 1002-1008.
Fang et al., 2002, "Free radicals, antioxidants, and nutrition." *Nutrition* 18 (10): 872-879.
Flora et al., 2003, "Beneficial effect of combined administration of some naturally occurring antioxidants (vitamins) and thiol chelators in the treatment of chronic lead intoxication." *Chemico-Biological Interactions* 145: 267-280.
Garcia-Ruiz et al., 1995, "Feeding S-adenosyl-L-methionine attenuates both ethanol-induced depletion of mitochondrial glutathione." *Hepatology* 21(1): 207-14.
Graham et al., 1989, "Reduced glutathione effecs on α-Tocopherol concentration of rat liver microsomes undergoing NADPH-dependent lipid peroxidation." *Lipids* 24 (11): 909-914.
Guarino et al., 2003, "Hepatic glutathione and nitric oxide are critical for hepatic insulin-sensitizing." *Am J Phiol Gastrointest-Liver-Physiol* 284 (4): G588-94.
Halim et al., 1997, "Biochemical effect of antioxidants on lipids and liver function in experimentally-induced liver damage." *Ann Clin Biochem* 34: 656-663.
Jaeschke et al., 1988, "Reactive oxygen species during ischemia-reflow injury in isolated perfused rat liver." *J. Clin Invest.* 81(4): 1240-6.
Jaeschke et al., 2003, "The role of oxidant stress and reactive nitrogen species in acetaminophen hepatotoxicity." *Toxicology Letters* 144:279-288.
Lautt et al., 1998, "Rapid insulin sensitivity test (RIST)." *Can. J. Physiol. Pharamcol.* 76:1080-1086.
Lautt et al., 1999, "The HISS story overview: a novel hepatic neurhumoral regulation of peripheral insulin sensitivity in health and diabetes." *Can. J. Physiol. Pharamcol.* 77: 553-562.
Lautt, 2003, "Practice and principles of pharmacodynamic determination of HISS-dependent and HISS-independent insulin action: Methods to quantitate mechanisms of insulin resistance." *Medicinal Research Reviews* 23(1): 1-14.
Lautt, 2004, "A new paradigm for diabetes and obesity: the hepatic insulin sensitizing substance (HISS) hypothesis." *J. Pharmacol. Sci.* 95: 9-17.
Lieber et al., 1990, "S-adenosyl-L-methionine attenuates alcohol-induced liver injury in the baboon." *Hepatology* 11(2): 165-72.
Lieber, 1999, "Role of S-adenosyl-L-methionine in the treatment of liver diseases." *Journal of Hepatology* 30: 1155-1159.
Locatelli et al., 2003, "Oxidative stress in end-stage renal disease: an emerging threat to patient outcome." *Nephrol Dial Transplant* 18: 1272-1280.
Mato et al., 1999, "S-Adenosylmethionine in alcoholic liver cirrhosis: a randomized, placebo-controlled, double-blind, multicenter clinical trial." *Journal of Hepatology* 30: 1081-1089.
McDonough, 2003, "Antioxidant nutrients and alcohol." *Toxicology* 189: 89-97.

(Continued)

*Primary Examiner* — Kevin E Weddington
(74) *Attorney, Agent, or Firm* — Merchant & Gould P.C.

(57) ABSTRACT

The present invention provides antioxidant compositions comprising S-adenosylmethionine (SAMe), vitamin E and vitamin C and uses thereof for the treatment of liver injury and insulin resistance.

14 Claims, 4 Drawing Sheets

(56) References Cited

OTHER PUBLICATIONS

Parola et al., 1992, "Vitamin E dietary supplementation protets against carbon tetrachloride-induced chronic liver damage and cirrhosis." *Hepatology* 16(4): 1014-21.

Scholz et al., 1997, "Glutathione-dependent factors and inhibition of rat liver microsomal lipid peroxidation." *Free Radical Biology & Medicine* 23(5): 815-828.

Singh et al., 1994, "Plasma levels of antioxidant vitamins and oxidative stress in patients with acute myocardial infarction." *Acta Cardiologica* 49(5): 441-452.

Stehbens et al., 2003, "Oxidative stress, toxic hepatitis, and antioxidants with particular emphasis on zinc." *Exp Mol Pathol* 75: 265-276.

Vendemiale et al., "An update on the role of free radicals and antioxidant defense in human disease." *Int. J. Clin. Lab. Res.* 29: 49-55.

Faure et al., "Vitamin E improves free radical defense system potential and insulin sensitivity of rats fed high fructose diets," *The Journal of Nutrition* (1997) 127 (1): 103-107.

\* cited by examiner

USE OF S-ADENOSYLMETHIONINE, VITAMIN E, AND VITAMIN C FOR THE TREATMENT OF OXIDATIVE LIVER INJURY

This application is a Divisional Application of Ser. No. 11/814,866, filed 21 May 2008 in the United States, which is a National Stage Application of PCT/CA2006/000108, filed 26 Jan. 2006, which claims benefit of Ser. No. 60/646,594, filed 26 Jan. 2005 in the United States and which applications are incorporated herein by reference. To the extent appropriate, a claim of priority is made to each of the above disclosed applications.

FIELD OF INVENTION

The present invention relates to compositions comprising antioxidants and uses thereof, and in particular, use in the treatment of liver injury.

BACKGROUND

Oxidative stress has been implicated in the pathogenesis of acute and chronic liver injury in a variety of pathophysiological conditions such as hepatotoxin exposures, intrahepatic cholestasis, alcoholic liver injury, liver ischemia/reperfusion injury and viral hepatitis (Stehbens W E. Exp Mol Pathol. 2003; 75(3): 265-76. Jaeschke H et al. Toxicol-Lett. 2003; 144(3): 279-88. McDonough K H. Toxicology. 2003; 189(1-2): 89-97. Jaeschke H et al. J Clin Invest. 1988; 81(4): 1240-6). Overproduction of reactive oxygen species (ROS) and nitrogen species (RNS), along with significant decrease of antioxidant defense in these pathological conditions, impairs various cellular functions through the processes of lipid peroxidation, protein oxidation and nucleic base oxidation. Lipid peroxidation, for example, causes changes in the physical and chemical properties of cellular membranes, thus altering their fluidity and permeability, leading to impairment in membrane signal transduction and ion exchange, resulting in swelling, cytolysis and finally cell death. The oxidation of proteins and DNA also relates directly to cellular dysfunction and death (Fang Y Z et al. Nutrition. 2002; 18(10): 872-9).

Accordingly, effects of antioxidants or free radical scavengers have been widely tested for the prevention and treatment of acute and chronic liver injuries. In some of those studies, antioxidants have shown beneficial effects, specifically for prevention and treatment of chronic liver injury (Parola M et al. Hepatology. 1992;16(4):1014-21. Halim A B, et al. Ann Clin Biochem. 1997; 34 (Pt 6):656-63. Garcia-Ruiz C, et al. Hepatology. 1995; 21(1):207-14. Mato J M et al. J Hepatol. 1999; 30(6):1081-9. Lieber et al. Hepatology. 1990; 11(2): 165-72. Bruck R et al. J Hepatol. 2001; 35(4): 457-64. Bruck R et al. J Hepatol. 2004; 40(1): 86-93). However, the efficacy of antioxidant treatment in acute liver injury with a single antioxidant has been less clear (Baron V et al. Biochim Biophys Acta. 1999; 1472(1-2):173-80). Currently available antioxidant treatments are deficient for the treatment of acute liver injury. Furthermore, currently available antioxidant therapies do not address secondary events resulting from the injury such as insulin resistance.

SUMMARY OF INVENTION

In a first aspect, the invention provides a pharmaceutical composition comprising: (a) S-adenosylmethionine, a derivative or pharmaceutically acceptable salt thereof, (b) vitamin E, a derivative or pharmaceutically acceptable salt thereof, (c) vitamin C, a derivative or pharmaceutically acceptable salt thereof, and (d) a pharmaceutically acceptable carrier.

In a second aspect, the invention provide use of a therapeutically effective amount of S-adenosylmethionine, a derivative or pharmaceutically acceptable salt thereof in combination with a therapeutically effective amount of vitamin E, a derivative or pharmaceutically acceptable salt thereof, and of vitamin C, a derivative or pharmaceutically acceptable salt thereof, for treatment of oxidative liver injury in a patient in need thereof.

In a third aspect, the invention provides use of a therapeutically effective amount of S-adenosylmethionine, a derivative or pharmaceutically acceptable salt thereof in combination with a therapeutically effective amount of vitamin E, a derivative or pharmaceutically acceptable salt thereof, and of vitamin C, a derivative or pharmaceutically acceptable salt thereof, for treatment of insulin resistance in a patient in need thereof.

In a fourth aspect, the invention provides use of S-adenosylmethionine, a derivative or a pharmaceutically salt thereof in combination with vitamin E, a derivative or pharmaceutically acceptable salt thereof, and vitamin C, a derivative or pharmaceutically acceptable salt thereof for the preparation of a medicament for treating liver injury wherein said medicament comprises a therapeutically effective amount of S-adenosylmethionine, vitamin E, vitamin C, derivatives or pharmaceutically acceptable salts thereof.

In a fifth aspect, the invention provides use of S-adenosylmethionine, a derivative or pharmaceutically acceptable salt thereof, vitamin E, a derivative or pharmaceutically acceptable salt thereof, and vitamin C, a derivative or pharmaceutically acceptable salt thereof, for the preparation of a medicament for treating insulin resistance, wherein said medicament comprises a therapeutically effective amount of the S-adenosylmethionine, vitamin E, vitamin C, derivatives or pharmaceutically acceptable salts thereof.

In a sixth aspect, the invention provides a method of treating oxidative liver injury comprising administering a therapeutically effective amount of S-adenosylmethionine, a derivative or a pharmaceutically salt thereof in combination with a therapeutically effective amount of vitamin E, a derivative or pharmaceutically acceptable salt thereof, and vitamin C, a derivative or pharmaceutically acceptable salt thereof, to a patient in need thereof.

In a seventh aspect, the invention provides a method of treating insulin resistance comprising administering a therapeutically effective amount of S-adenosylmethionine, a derivative or a pharmaceutically salt thereof in combination with a therapeutically effective amount of vitamin E, a derivative or pharmaceutically acceptable salt thereof, and vitamin C, a derivative or pharmaceutically acceptable salt thereof, to a patient in need thereof.

In an eighth aspect, the invention provides a kit comprising: a composition comprising S-adenosylmethionine, a derivative or pharmaceutically acceptable salt thereof, vitamin E, a derivative or pharmaceutically acceptable salt thereof and vitamin C and instructions for use of composition in the treatment of oxidative liver injury or insulin resistance.

In a ninth aspect, the invention provides a kit comprising individual dosage units of S-adenosylmethionine, a derivative or pharmaceutically acceptable salt thereof, vitamin E, a derivative or pharmaceutically acceptable salt thereof and vitamin C, a derivative or pharmaceutically acceptable salt thereof and instructions and instructions for use of said dosage units in the treatment of oxidative liver injury or insulin resistance.

DETAILED DESCRIPTION

The efficacy of currently available single antioxidant therapies in treating acute liver injuries is poor. The present invention provides a novel combination antioxidant therapy for the treatment of liver injury, and in particular acute liver injury resulting from oxidative stress.

While the invention is not limited to any particular theory, the inventors believe that the major reason behind the poor efficacy observed with single antioxidant therapies is that, while the production of the free radicals with various chemical properties in acute and chronic liver injury is widely spread throughout the different tissue and cellular components, the chemical property of an individual antioxidant can only allow it to scavenge the free radicals located in a specific cellular component, e.g., lipid or aqueous phase. Moreover, the efficacy of an antioxidant substance is also dependent on the redox state of the cell. In situations that an imbalanced redox state pre-existed, antioxidant treatment will be less, or none, effective (Flora S J et al. Chem Biol Interact. 2003; 145(3):267-80. Scholz R W et al. Free Radic Biol Med. 1997; 23(5): 815-28. Graham K S et al. Lipids, 1989; 24(11): 909-14). It has been suggested recently that the therapeutic strategy for protecting against oxidative stress will be to target simultaneously the free radicals in both the lipid and aqueous phases, in extracellular and intracellular spaces (Vendemiale G et al. Int J Clin Lab Res. 1999; 29(2): 49-55).

The present inventors have determined that combined antioxidative treatment with S-adenosylmethionine (SAMe), vitamin E and vitamin C provides synergistic antioxidative effects and protects the liver from injury induced by oxidative stress. The inventors are the first to use SAMe, vitamin E and vitamin C in combination for the treatment of oxidative liver injury. All three compounds play an important and different role in scavenging free radicals (Fang Y Z et al. Nutrition. 2002; 18(10): 872-9). The water-soluble property of vitamin C makes it the first order antioxidant to protect cell components from free radical-induced damage by quenching various water-soluble radicals, e.g. superoxide anion, in the aqueous phase. Vitamin E is a lipid-soluble molecule and can transfer its phenolic hydrogen to a peroxyl free radical of a peroxidized polyunsaturated fatty acid, thereby breaking the radical chain reaction thus preventing the lipid peroxidation in cellular and subcellular membrane phospholipids, especially those of mitochondria and microsomes. SAMe is a natural, non-toxic regulator of glutathione (GSH) with good bioavailability (Lieber C S. Hepatol. 1999; 30(6):1155-9). GSH is the main intracellular defense against free radicals. GSH stores are significantly depleted in liver injury induced by oxidative stress. Administration of SAMe represents an effective way to restore intracellular GSH stores, especially in mitochondria, thus improving the cellular ability to scavenge free radicals (Lieber C S. Hepatol. 1999; 30(6):1155-9).

The present inventors have determined that combination antioxidant therapy with S-adenosylmethionine (SAMe), vitamin E and vitamin C is useful for treating both acute and chronic liver injury induced by oxidative stress. The present inventors have also determined that the combination antioxidant therapy of the invention is useful for treating secondary events related to or resulting from the liver injury. Such secondary events include the impairment of insulin sensitivity.

In response to insulin administered in the fed state, the liver is suggested to release a putative hormone, hepatic insulin sensitizing substance (HISS), to stimulate glucose uptake in skeletal muscle (Lautt W W et al. Can J Physiol Pharmacol. 1998; 76(12): 1080-6. Lautt W W et al. Can 3 Physiol Pharmacol. 1999; 77(8): 553-62. Lautt W W et al. Med Res Rev. 2003; 23(1): 1-14. Lautt W W. J Pharmacol Sci. 2004; 95(1): 9-17.). HISS is responsible for approximately 55% of the glucose disposal effect of an injection of insulin and this portion of insulin response is termed HISS-dependent insulin sensitivity. Blockade of HISS action results in HISS-dependent insulin resistance (HDIR). HDIR is seen in a wide variety of pathological models including the spontaneously hypertensive rat, sucrose fed rats, adult offspring of fetal alcohol exposure, acute stress and ageing, physical interruption of hepatic parasympathetic nerves, and pharmacological blockade of hepatic muscarinic cholinergic receptors or nitric oxide production or cyclooxygenase (for review, see Lautt W W et al. Can J Physiol Pharmacol. 1999; 77(8): 553-62; Lautt W W et al. Med Res Rev. 2003; 23(1): 1-14; and Lautt W W. J Pharmacol Sci. 2004; 95(1): 9-17).

Liver injury is known to impact the release of hepatic insulin sensitizing substance (HISS). It has been demonstrated that the ability of the liver to release HISS is severely impaired in situations such as hepatic parasympathetic dysfunction and chronic bile duct ligation. The insulin resistance' caused by bile duct ligation is due to absence of HISS action; mimicking the normal parasympathetic nerve function with intraportal acetylcholine restores insulin action to normal levels (Lautt W W. J. Pharmacol Sci. 2004; 95(1): 9-17.). The mechanism that causes the HISS-dependent insulin resistance is currently unclear but may be related to the decrease in hepatic GSH content and to the unbalanced production of nitric oxide and $O_2$-. It has been demonstrated by Guarino et al (Guarino M P et al. Am J. Physiol Gastrointest-Liver-Physiol. 2003; 284(4): G588-94) that reduction in HISS-dependent insulin sensitivity can be caused by depletion of hepatic GSH and reduced production of S-nitrosoglutathione.

The present inventors have now determined that combination antioxidant therapy comprising SAMe, vitamin E and vitamin C decreases the severity of HISS dependent insulin resistance following oxidative liver injury. The inventors have also determined that the rapid insulin sensitivity test ("RIST") is especially useful for assessing liver injury. Traditionally, evaluation of liver function is achieved by assessing the activities of hepatic enzymes in plasma, such as the activities of ALT and AST. This is an indirect method since the change in enzyme activities in plasma is only reflecting the amount of enzymes that leak out from the membrane of damaged hepatocytes, rather than a change in "real liver function". The inventors have previously disclosed the use of RIST for evaluating insulin sensitivity. The inventors have now determined that the RIST index can be used as an index to evaluate liver function in injured liver and that the RIST index is preferable to hepatic enzyme alterations in the assessment of liver function since the latter is relatively quiescent in chronic liver diseases.

As used herein, the term S-adenosylmethionine (SAMe) includes derivatives, conjugates and metabolites of S-adenosylmethionine and pharmaceutically acceptable salts thereof (see for example, U.S. Pat. Nos. 3,893,999 and 4,057,686). S-adenosylmethionine and its salt forms may be natural, semisynthetic, bioengineered, synthetic or extracted, or any combination thereof.

As used herein, the term "vitamin E" includes alpha, beta, gamma, and delta-tocopherols and their derivatives, conjugates and metabolites. The vitamin E may also be a combination of alpha, beta, gamma, and delta-tocopherols. The alpha-form occurs naturally as the d-isomer known as d-α-tocopherol (d-2,5,7,8-tetramethyl-2-(4',8',12'-trimethyltridecyl)-6-chromanol). Other forms of vitamin E which can be used include: d-α-tocopheryl acetate, d-α-tocopheryl succinate, d-α-tocopheryl nicotinate and d-α-tocopheryl linoleate.

Also the corresponding dl forms may be used which include: dl-α-tocopherol, dl-α-tocopheryl acetate, dl-α-tocopheryl succinate, dl-α-tocopheryl nicotinate and dl-α-tocopheryl linoleate and their derivatives, conjugates and metabolites.

As used herein, the term "vitamin C" includes ascorbic acid and its derivatives, conjugates and metabolites. Such derivatives include, for example, oxidation products such as dehydroascorbic acid and edible salts of ascorbic acid such as, illustratively, calcium, sodium, magnesium, potassium and zinc ascorbates. The term vitamin C includes these derivatives and any other art-recognized vitamin C derivatives (see for example, U.S. Pat. Nos. 5,137,723 and 5,078,989) including vitamin C esters, useful for the purposes of this invention.

In a first aspect, the invention provides a pharmaceutical composition comprising: S-adenosylmethionine, vitamin E, vitamin C and a pharmaceutically acceptable carrier. The S-adenosylmethionine, vitamin E, or vitamin C may be in the form of a suitable pharmaceutically acceptable salt. Functional derivatives, conjugates and metabolites of S-adenosylmethionine, vitamin E, or vitamin C can also be used to prepare the pharmaceutical composition according to the invention.

The pharmaceutical compositions of the present invention may further comprise pharmaceutically acceptably liver-targeting compounds. The inclusion of a liver-targeting compound allows the pharmaceutical compositions to be targeted to the liver of the patient thereby eliminating deleterious systemic effects. The S-adenosylmethionine, vitamin E, and vitamin C can be conjugated to bile salts or albumin for preferential delivery to the liver. Alternatively, the S-adenosylmethionine, vitamin E, vitamin C can be encapsulated within liposomes which are preferentially targeted to the liver.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/orpolyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The pushfit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e. g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Capsules and cartridges of e. g. gelatin for use in an inhaler or insufflator may be formulated containing a powder mix of the compound and a suitable powder base such as lactose or starch.

The compounds may be formulated for parenteral administration by injection, e. g., by bolus injection or continuous infusion. Formulations for injection may be presented in unit dosage form, e. g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e. g., sterile pyrogen-free water, before use.

The compounds may also be formulated in rectal compositions such as suppositories or retention enemas, e. g., containing conventional suppository bases such as cocoa butter or other glycerides.

In addition to the formulations described previously, the compounds may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a co-solvent system comprising benzyl alcohol, a nonpolar surfactant, a water-miscible organic polymer, and an aqueous phase. Naturally, the proportions of a co-solvent system may be varied considerably without destroying its solubility and toxicity characteristics. Furthermore, the identity of the co-solvent components may be varied.

Alternatively, other delivery systems for hydrophobic pharmaceutical compounds may be employed.

Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients.

Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

Suitable routes of administration may, for example, include oral, rectal, transmucosal, transdermal, or intestinal administration; parenteral delivery, including intramuscular, subcutaneous, intramedullary injections, as well as intrathecal, direct intraventricular, intravenous, intraperitoneal, intranasal, or intraocular injections.

In another aspect, the invention provides the use of S-adenosylmethionine, vitamin E, vitamin C for treatment of oxidative liver injury. The oxidative liver injury may be either acute or chronic. In a preferred embodiment of the invention, the liver injury to be treated is induced by exposure to free radicals. In further aspect, the invention provides the use of adenosylmethionine, vitamin E, vitamin C for treatment of insulin resistance and more preferably HISS dependent insulin resistance.

The methods of treating oxidative liver injury and insulin resistance according to the invention comprise the administration of a therapeutically effective amount of S-adenosylmethionine, vitamin E, vitamin C to a patient in need thereof.

By an "effective amount" or a "therapeutically effective amount" of a pharmacologically active agent is meant a nontoxic but sufficient amount of the drug or agent to provide the desired effect. In a combination therapy of the present invention, an "effective amount" of one component of the combination is the amount of that compound that is effective to provide the desired effect when used in combination with the other components of the combination. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation.

The therapeutic effective amount of any of the active agents encompassed by the invention will depend on number of factors which will be apparent to those skilled in the art and in light of the disclosure herein. In particular these factors include: the identity of the compounds to be administered, the formulation, the route of administration employed, the patient's gender, age, and weight, and the severity of the condition being treated and the presence of concurrent illness affecting the gastro-intestinal tract, the hepatobiliary system and the renal system. Methods for determining dosage and toxicity are well known in the art with studies generally beginning in animals and then in humans if no significant animal toxicity is observed. The appropriateness of the dosage can be assessed by monitoring insulin resistance and liver function using the RIST protocol as set out in Lautt et al, 1998. Where the dose provided does not cause insulin resistance to decline to normal or tolerable levels, following at least three days of treatment, the dose can be increased. The patient should be monitored for signs of adverse drug reactions and toxicity, especially with regard to liver function.

For administration to mammals, and particularly humans, it is expected that the daily dosage level of each of S-adenosylmethionine, vitamin E, vitamin C will be from 0.1 mg/kg to 1000 mg/kg, typically between 10 mg/kg and 100 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In a preferred embodiment of the invention, the therapeutically effective amount of the: S-adenosylmethionine is between 5 and 50 mg/kg, vitamin C is between 10 and 200 mg/kg and vitamin E is between 10 and 500 mg/kg.

The therapeutically effective amounts may be administered in various combinations in which the components may be present in a single dosage unit or in more than one dosage unit. For example, the combinations of the present invention may be administered in a single daily dosage unit in which all components are present, e.g., in a single capsule or tablet. The doses may also be administered in combinations of more than one dosage unit in which each dosage unit contains at least one component or in which two or more components are combined into a single dosage unit. For example, a combination of S-adenosylmethionine, vitamin E and vitamin C may be administered as a pill, capsule or tablet of SAMe and a separate pill, tablet or capsule of ergothioneine. A combination of S-adenosylmethionine, vitamin E and vitamin C may include each component in a separate dosage unit, or two of the components in one dosage unit, such as combined in the same capsule and the other component in a separate dosage unit, or, as explained above, all three of the components in the same (i.e., a single) dosage unit. These combinations may be provided in kits or blister packs, in which more than one dosage unit of the various components are provided in the same package or container, for co-administration to a human or animal. For example, a single dosage unit (such as for example, a tablet, a capsule) of each of S-adenosylmethionine, vitamin E and vitamin C may be placed in the same blister pack along with instructions for co-administration. These combinations may be provided, for example, in kits, blister packs, packets or bottles shrink-wrapped together in which more than one dosage unit of the various components are provided in the same dispensing unit for co-administration to a human or animal.

Although the invention has been described with reference to illustrative embodiments, it is to be understood that the invention is not limited to these precise embodiments, and that various changes and modifications may be effected therein by one skilled in the art. All such changes and modifications are intended to be encompassed in the appended claims.

EXAMPLE ONE

SAMe, Vitamin E and Vitamin C Combination Therapy Improves Liver Function in a Rat Model of Acute Liver Injury Materials and Methods Surgical Preparation. Male Sprague-Dawley rats weighing 260-300 g from the University of Manitoba colony were maintained in the animal house under controlled conditions (22±1° C., 12 h light/12 h dark cycle). They were fed a standard rat chow diet with free access to water. All rats underwent a fasting period of 8 h and a refeeding phase of 2 h immediately before the start of surgical preparation. As HISS is only released in the fed state, the fasting-refeeding protocol assured a high level of HISS release in response to insulin. The rats were anaesthetized with an intraperitoneal injection of sodium pentobarbital (65 mg kg-1; Somnotol, MTC Pharmaceuticals, Ont). Maintained anesthesia was achieved throughout the experiment by a continuous infusion of pentobarbital sodium (0.5 mg.ml-1 saline given at 50 µl.min-1) through a cannula in the jugular vein, supplemented with a 0.65 mg (0.01 ml) bolus injection when required. The rats were placed on a temperature-controlled surgical table (Harvard Apparatus, Kent, England) and rectal temperature was monitored and held at 37-37.5° C. Spontaneous respiration was allowed through a tracheal tube.

An arterial-venous shunt was established, as previous described (Lautt W W et al. Can J Physiol Pharmacol. 1998; 76(12): 1080-6.), for monitoring mean arterial blood pressure (MAP), blood glucose level and for drug delivery. Briefly, two catheters (polyethylene tubing PE60), one inserted into the right femoral artery and the other into the right femoral vein, were connected to the two openings of a three way vascular circuit consisting of a T tube connected with silicon tubing. The third opening of the circuit was connected to a pressure transducer for the recording of the shunt pressure which, when the silicon tubing toward the venous side of the circuit was closed by clamping, represented the systemic arterial blood pressure. Blood samples were taken from the arterial side of the shunt for the glucose measurement. Flowing blood within the shunt assures the real time measurement of the blood glucose concentration, which is essential for the euglycemic clamp test as mentioned below. An infusion line was inserted into the venous side of the loop for drug delivery. Another infusion line connected to the jugular vein was established for glucose infusion. Animals were heparinized (100 IU.kg-1) to prevent clotting in the vascular loop.

Rapid Insulin Sensitivity Test (RIST). The RIST was performed as previously described (Lautt W W et al. Can J Physiol Pharmacol. 1998; 76(12): 1080-6.). Briefly, following completion of surgery, animals were allowed a 30-min stabilization period. The baseline glucose levels were then determined by samples taken at 5-min intervals and continued until three successive stable determinations were made. The mean of these three data points is regarded as the baseline for the RIST. To perform the RIST, human insulin (50mU.kg-1 in 0.5 ml saline) was infused into the femoral vein at the rate of 0.1 ml.min-1 for 5-min. After 1-min of insulin infusion, the first test glucose sample was determined and a variable glucose infusion (10%) was initiated. Blood samples were taken every 2-min and the glucose infusion rate was adjusted accordingly to maintain euglycemia. The RIST index is the amount of glucose (mg.kg-1) infused, to maintain euglycemia, over the test period that terminated when no further glucose infusion was required (approximately 30 min). At the end of a RIST, the animal is at its pretest glycemic level.

Animal groups. Six groups of animals were established under the following treatments: (1): Normal control rats, treated with saline and corn oil injection at the dose of 2 and 1 ml.kg-1, respectively, n=12. (2): Normal rats, treated with Vitamin C, Vitamin E and SAMe, n=8. The dose for Vitamin C and Vitamin E were 100 and 200 mg.kg-1, respectively; for SAMe was 25 mg.kg-1. (3): Thioacetaminde (TAA) rats, given with intraperitoneal injection of TAA at the dose of 200 mg.kg-1, n=9. (4): TAA rats treated with Vitamin C+Vitamin E, n=11. (5): TAA rats with SAMe treatment, n=7. (6): TAA rats treated with Vitamin C+Vitamin E+SAMe, n=8. All compounds were administered by intraperitoneal injection (i. p.). TAA was administered 24 h before the start of surgery, and all treatment with vitamins and SAMe were given 1 h post TAA administration.

Protocol. Two RIST tests were performed for each rat. Following the establishment of glucose baseline, the first RIST index was determined and this was regarded as the control RIST. The rats were allowed to achieve stabilized glucose baseline again and the second RIST was performed after blockade of HISS formation with intravenous infusion of atropine (0.1 mg.kg-1 in 0.5ml saline, 0.1 ml.min-1). The first RIST index includes the effects of both HISS-dependent and HISS-independent components, and the second RIST index represents only the HISS-independent component (Lautt W W et al. Can J Physiol Pharmacol. 1999; 77(8): 553-62. Lautt W W et al. Med Res Rev. 2003; 23(1): 1-14.). The percentage contribution of HISS-dependent component to total insulin sensitivity was calculated as: % HISS=(RIST index in control−RIST index after atropine)/RIST index in control. At the end of the experiment, 1 ml blood was withdrawn from the femoral artery. The blood was centrifuged ($1.4 \times 10^4$ rpm for 5-min, Eppendorf Centrifuge 5414C, Brinkmann Instruments, N.Y.) and the plasma was kept at −20 °C. for further hepatic enzymes analysis.

Hepatic enzymes analysis. Serum samples from rats in groups 1 to 6 were analyzed for alanine aminotransferase (ALT) and aspartate aminotransferase (AST) activities spectrophotometrically utilizing an Abbott analyzer and Diagnostic Chemicals Limited assay reagents (Charlottetown, P.E.I, Canada).

Liver histopathological examination. The left liver lobe was excised and embedded in paraffin, sliced 7 μm in thickness, and stained with hematoxylin-eosin. The tissue slices were then analyzed with light microscopy. Histopathological analysis of the injured area was performed with a computerized video-imaging system (Image-Pro Plus. Media Cybernetics, Md., USA) by a pathologist (Y.F.) who was not aware of sample assignment to experimental group. The degree of injury, including inflammation, necrosis and bridging necrosis, was expressed as the mean of 5 different fields for each slide scaled as 0-3: normal-0, mild-1, moderate-2 and severe-3.

Data collection, Instruments and Chemicals. A PowerLab recording unit, together with a computer application software (AD Instruments Pty Ltd, Australia), was used to record and analyze the mean arterial blood pressure. Blood glucose concentration was measured by a glucose analyzer (Yellow Springs Instrument, Yellow Springs, Ohio). The infusion pumps were from Kent Scientific Corporation, Torrington, Conn. (Model RS 232).

Human insulin was purchased from Eli Lilly and Company (Toronto, Ont.). Vitamin C (L-Ascorbic acid), Vitamin E ((±)-α-Tocopherol), SAMe and TAA were all purchased from Sigma. Insulin, vitamin C and TAA were dissolved in saline. SAMe was dissolved in cold saline. Vitamin E was dissolved in corn oil.

Statistical analysis. Values are presented as means±SE. The data were analyzed by paired or unpaired t-test where appropriate. A one-way ANOVA followed by Tukey's test was employed when the multiple means from different groups were compared. Statistical significance was taken at $p<0.05$.

Results

Figure 1:
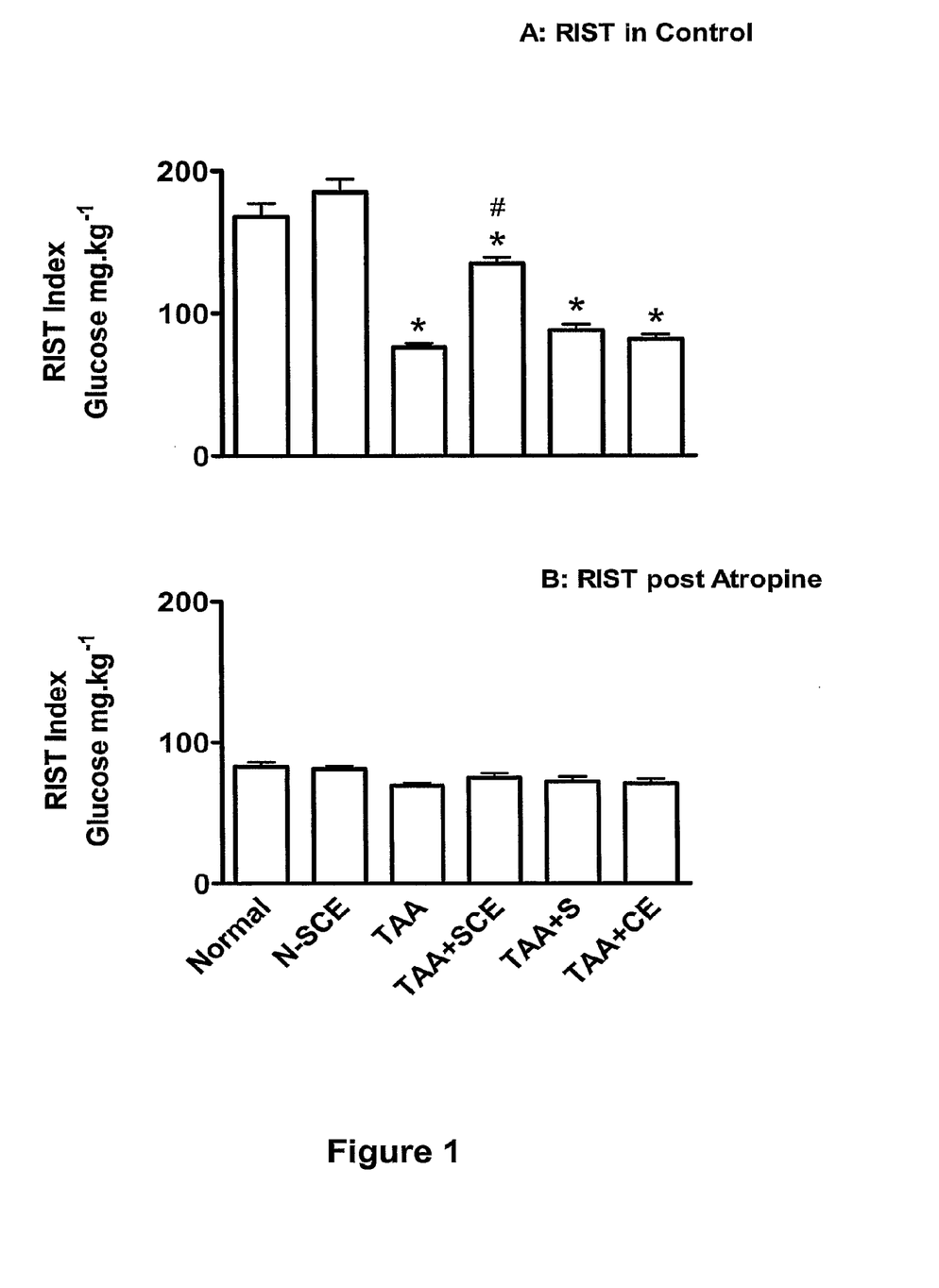
FIG. 1 comprises bar graphs illustrating the RIST index in control rats (A, top panel) and rats treated with atropine (B, top panel). Abbreviations—Normal: normal rats; N-SCE: normal rats treated with SAMe+Vitamins E and C; TAA: rats with thioacetamide-induced liver damage; TAA+SCE, TAA+S and TAA+CE: rats with thioacetamide-induced liver damage treated with SAMe+vitamins C and E, with SAMe alone and with vitamins alone, respectively.

RIST in normal rats. Normal rats had a RIST index of 168.2±9.2 mg.kg$^{-1}$ (FIG. 1, A). Atropine at the dose of 0.1mg.kg$^{-1}$ did not change the basal glucose level (112.2±2.5 in control and 110.9±2.2 mg % post atropine) but significantly decreased the RIST index to 82.7±3.2 mg.kg$^{-1}$ (FIG. 1, B), representing a 50.0±2.1% inhibition of insulin sensitivity.

RIST in TAA rats. TAA at the dose of 200mg.kg$^{-1}$ significantly impaired insulin sensitivity. The RIST index was reduced to 75.5±2.8 mg.kg$^{-1}$, significantly lower than in normal rats ($p<0.01$, FIG. 1). Atropine did not further decrease the RIST index in TAA 200 rats as demonstrated by a similar RIST index of 69.0±2.1 mg.kg$^{-1}$, suggesting the impaired insulin sensitivity by TAA treatment resulted from the damage in HISS-dependent component. The basal glucose level was lower (96.5±3.0 mg %) in TAA 200 rats compared to their normal partners; however, the MAP (101±4.0 mmHg) remained in the same range as compared to the normal rats (106±3.5 mmHg).

Effect of combined treatment with SAMe+vitamin C+vitamin E on RIST in normal and TAA rats. Combined treatment of SAMe+vitamin C+vitamin E did not significantly influence the insulin sensitivity in normal rats, as demonstrated by a similar RIST index (185.6±9.2 mg.kg$^{-1}$, FIG. 1) compared to normal rats without treatments. However, this treatment significantly improved insulin sensitivity in TAA rats. As shown in FIG. 1, the treatment increased the RIST index to 134.6±4.6 mg.kg$^{-1}$. Although it was still lower than the RIST index compared to the normal rats, it was significantly higher than what was observed in TAA rats without treatment, suggesting a partial recovery in insulin sensitivity after the treatment. Further, blockade of HISS formation with atropine decreased the RIST index to 74.9±3.2 mg.kg$^{-1}$ in this group, or a decrease in insulin sensitivity by 44.4% (FIG. 3), which was close to the percent inhibition seen in normal rats after atropine (50%). The results suggest that the improved insulin sensitivity by combined treatment of SAMe+vitamin C+vitamin E is mainly due to the improvement in the HISS-dependent component.

Figure 2:
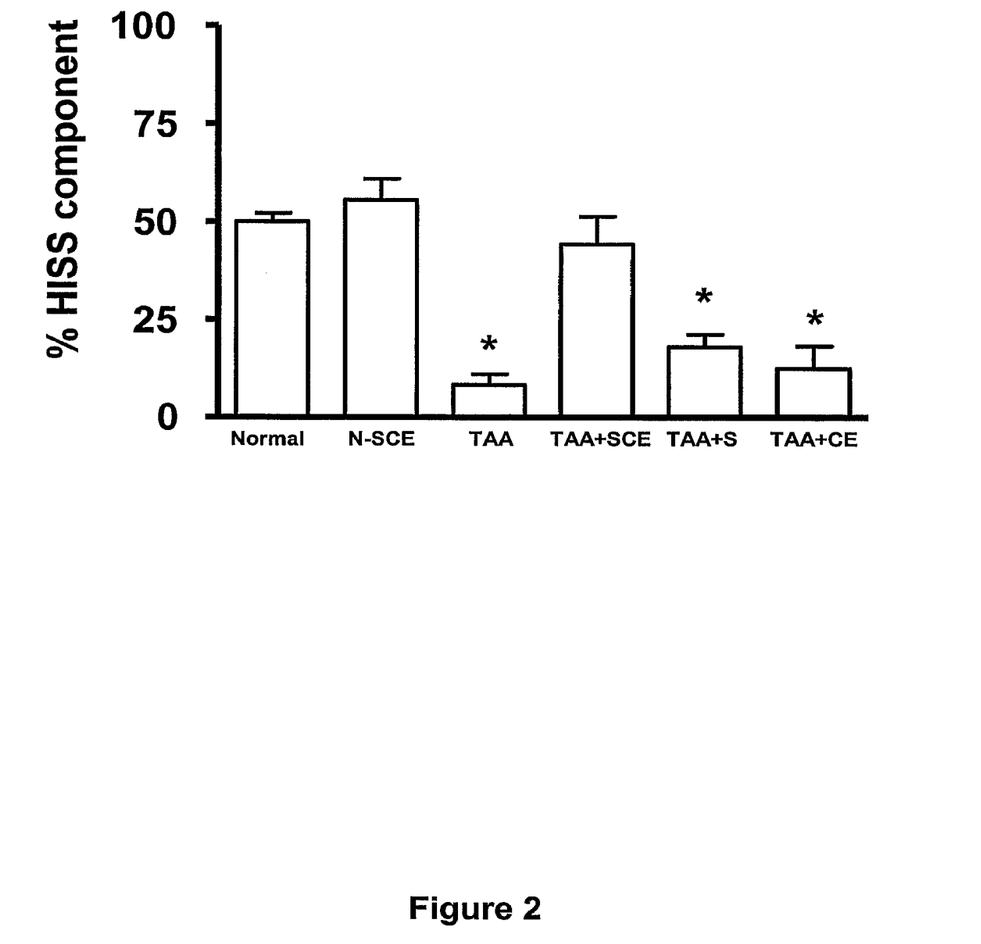
FIG. 2 is a bar graph illustrating the % HISS component in rats with different treatments. Abbreviations—Normal: normal rats; N-SCE: normal rats treated with SAMe+Vitamins E and C; TAA: rats with thioacetamide-induced liver damage; TAA+SCE, TAA+S and TAA+CE: rats with thioacetamide-induced liver damage treated with SAMe+vitamins C and E, with SAMe alone and with vitamins alone, respectively.

RIST in TAA rats treated with SAMe alone or a combination of vitamin C+vitamin E. TAA rats treated with SAMe alone had a RIST index of 88.0±4.1 mg.kg$^{-1}$, which was not different compared to the index from TAA rats without treatment (FIG. 1, 2). The RIST index post atropine (72.1±3.5 mg.kg$^{-1}$) in this group was also similar to TAA rats without treatment (FIG. 1, 2).

Similarly, TAA rats treated with a combination of vitamin C+vitamin E had a RIST index of 81.7±3.1 mg.kg$^{-1}$, which was not different compared to the index from TAA rats without treatment. The RIST index post atropine (70.7±3.4 mg.kg$^{-1}$) in this group was also similar to TAA rats without treatment (FIG. 1, 2).

Figure 3:
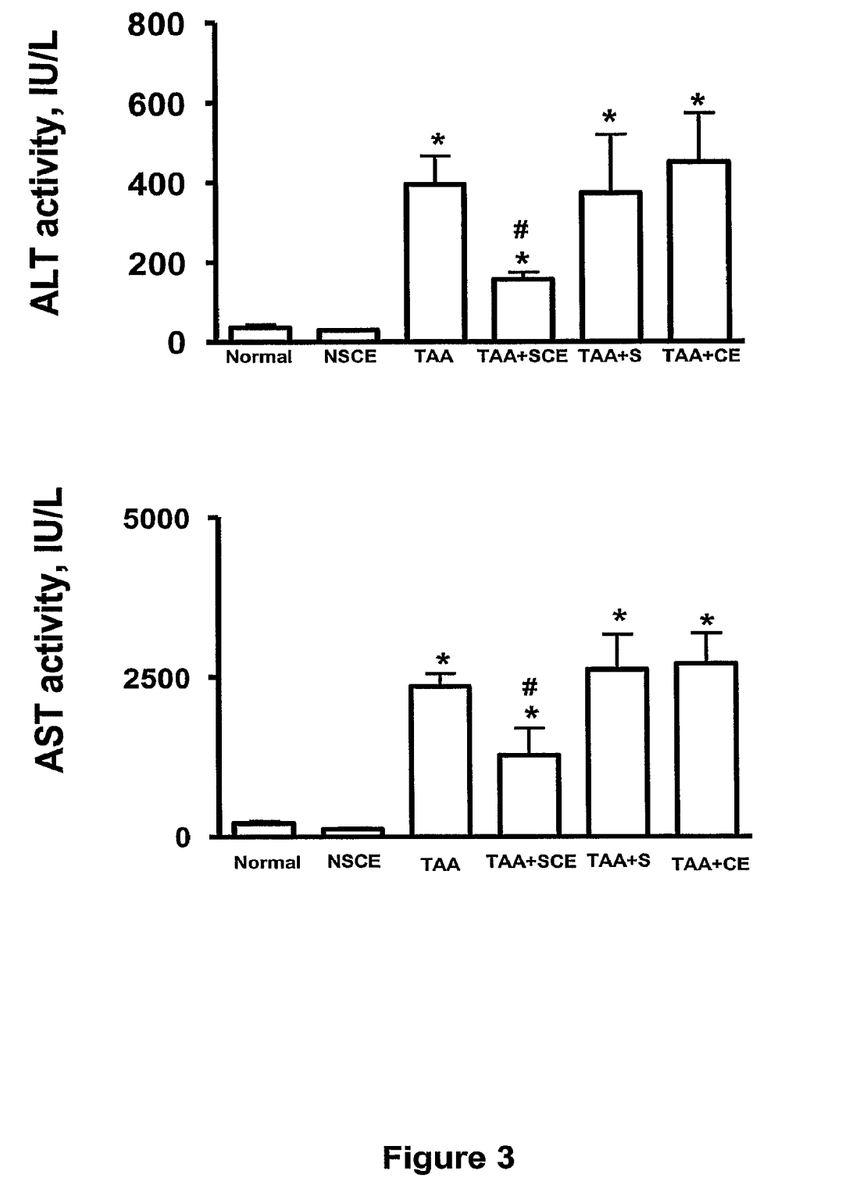
FIG. 3 comprises bar graphs illustrating serum alanine aminotransferase (ALT) (top panel) and aspartate aminotransferase (AST) (bottom panel) levels in rats with different treatment. Abbreviations—Normal: normal rats; N-SCE: normal rats treated with SAMe+Vitamins E and C; TAA: rats with thioacetamide-induced liver damage; TAA+SCE, TAA+S and TAA+CE: rats with thioacetamide-induced liver damage treated with SAMe+vitamins C and E, with SAMe alone and with vitamins alone, respectively.

Serum ALT and AST activities. As shown in FIG. 3, Animals treated with TAA showed a significant increase in ALT and AST activities. These increases were partially prevented when rats were treated with SAMe+vitamin C+vitamin E ($p<0.05$). In contrast, treatment with SAMe alone or vitamin C+vitamin E did not prevent the increases in these enzymes.

Figure 4:
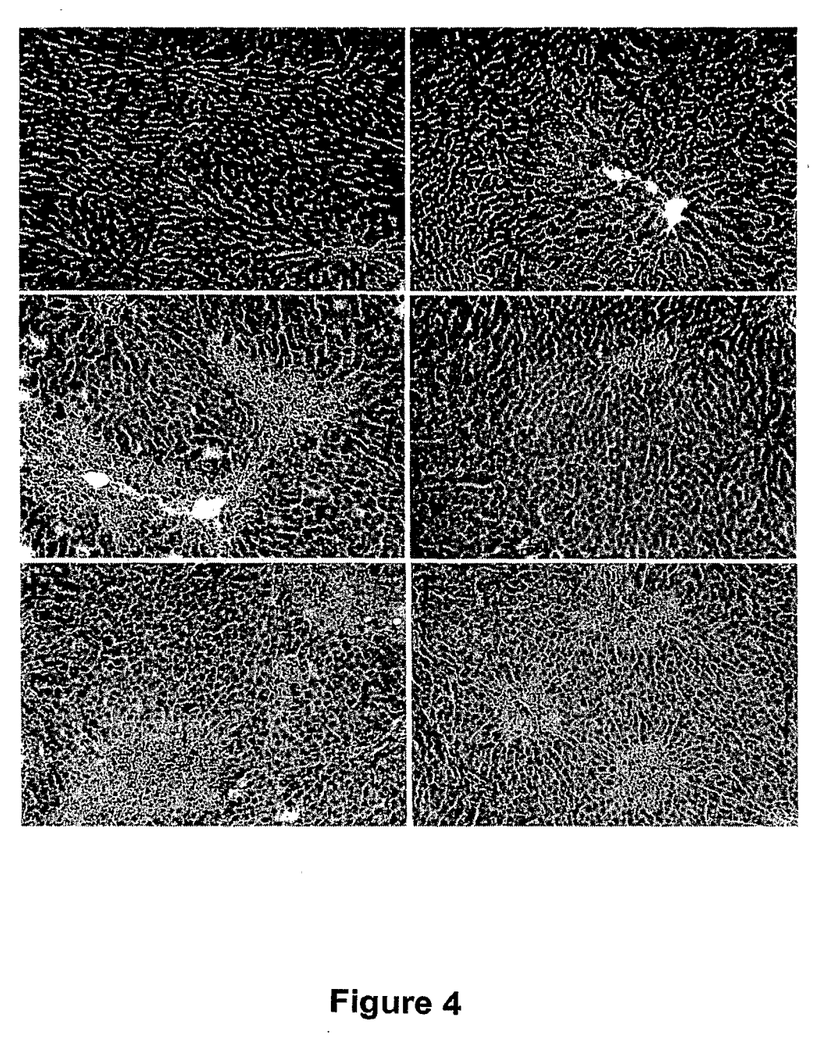
FIG. 4 comprises confocal microscope images of histological sections of liver from: (panel A) normal rat; (panel B) normal rat treated with SAMe+vitamins C and E; (panel C) TAA rat; (panel D) TAA rat treated with SAMe+vitamins C and E; (panel E) TAA rat treated with SAMe alone; (panel F) TAA rat treated with vitamins C and E.

Liver histopathology. Histological examination of livers in the TAA-treated rats revealed massive hepatocytic necrosis, including bridging necrosis, with influx of inflammatory cells. Treatment with SAMe alone or vitamin C+vitamin E showed a slight reduction in histological injury; in contrast, combined treatment with SAMe+vitamin C+vitamin E produced great reduction in histological injury (Table 1, FIG. 4).

TABLE 1

Effect of different treatments with SAMe, vitamin C and vitamin E on TAA-induced liver pathology.

| Rat Groups | Inflammation | Necrosis | Bridging Necrosis |
|---|---|---|---|
| Normal | 0.00 ± 0.00 | 0.00 ± 0.00 | 0.00 ± 0.00 |
| Normal + SCE | 0.00 ± 0.00 | 0.00 ± 0.00 | 0.00 ± 0.00 |
| TAA | 1.50 ± 0.22 | 2.33 ± 0.17 | 1.17 ± 0.36 |
| TAA + CE | 1.12 ± 0.17 # | 1.53 ± 0.13 ** ## | 0.08 ± 0.08 ** |

TABLE 1-continued

Effect of different treatments with SAMe, vitamin
C and vitamin E on TAA-induced liver pathology.

| Rat Groups | Inflammation | Necrosis | Bridging Necrosis |
|---|---|---|---|
| TAA + SAMe | 0.93 ± 0.13 * | 1.79 ± 0.15 * # | 0.09 ± 0.09 ** |
| TAA + SCE | 0.36 ± 0.05 ** | 0.74 ± 0.06 ** | 0.00 ± 0.00 ** |

* or ** P < 0.05 or 0.01 vs TAA
# or ## P < 0.05 or 0.01 vs TAA + SCE
Normal: normal rat; SAMe: S-adenosylmethionine; TAA: thioacetamide; TAA + CE, TAA + SAMe, TAA + SCE: liver injury induced by TAA treated by vitamins C and E, by SAMe and by SAMe plus vitamins C and E.

CONCLUSIONS

Acute liver injury by TAA severely reduced HISS-dependent insulin sensitivity, resulting in a decreased RIST index in TAA treated rats. The decrease in RIST index was due to decreased action of HISS since atropine, which blocks HISS action but not HISS independent direct insulin action (Lautt W W et al. Can J Physiol Pharmacol. 1999; 77(8): 553-62. Lautt W W et al. Med Res Rev. 2003; 23(1): 1-14. Lautt W W. J Pharmacol Sci. 2004; 95(1): 9-17.), did not further influence the RIST index in TAA-treated rats.

SAMe alone or vitamin E plus vitamin C did not show significant therapeutic efficacy. Combined treatment of SAMe with vitamin E plus C greatly improved liver function in a rat model of acute liver injury induced by TAA. In association with histological and enzymological alterations, HISS-dependent insulin sensitivity was severely impaired in rats that encountered oxidative liver injury induced by TAA and this impairment was greatly prevented by combined treatment of SAMe with vitamin E plus vitamin C.

What is claimed is:

1. A method of treating oxidative liver injury comprising administering a therapeutically effective amount of S-adenosylmethionine, a derivative or pharmaceutically acceptable salt thereof, vitamin E, a derivative or pharmaceutically acceptable salt thereof, and vitamin C, a derivative or pharmaceutically acceptable salt thereof to a patient in need thereof.

2. The method according to claim 1, wherein the oxidative liver injury is acute.

3. The method according to claim 1, wherein the oxidative liver injury is chronic.

4. The method according to claim 1, wherein the therapeutically effective amount of the S-adenosylmethionine, the derivative or pharmaceutically acceptable salt thereof, is between 0.1 and 1000 mg/kg.

5. The method according to claim 4, wherein the therapeutically effective amount of the S-adenosylmethionine, the derivative or pharmaceutically acceptable salt thereof, is between 10 and 100 mg/kg.

6. The method according to claim 5, wherein the therapeutically effective amount of the S-adenosylmethionine, the derivative or pharmaceutically acceptable salt thereof, is between 5 and 50 mg/kg.

7. The method according to claim 1, wherein the therapeutically effective amount of the vitamin C, the derivative or pharmaceutically acceptable salt thereof, is between 0.1 and 1000 mg/kg.

8. The method according to claim 7, wherein the therapeutically effective amount of the vitamin C, the derivative or pharmaceutically acceptable salt thereof, is between 10 and 200 mg/kg.

9. The method according to claim 8, wherein the therapeutically effective amount of the vitamin C, the derivative or pharmaceutically acceptable salt thereof, is between 10 and 100 mg/kg.

10. The method according to claim 1, wherein the therapeutically effective amount of vitamin E, the derivative or pharmaceutically acceptable salt thereof, is between 0.1 and 1000 mg/kg.

11. The method according to claim 10, wherein the therapeutically effective amount of vitamin E, the derivative or pharmaceutically acceptable salt thereof, is between 10 and 500 mg/kg.

12. The method according to claim 11, wherein the therapeutically effective amount of vitamin E, the derivative or pharmaceutically acceptable salt thereof, is between 10 and 100 mg/kg.

13. A kit comprising: a composition comprising S-adenosylmethionine, a derivative or pharmaceutically acceptable salt thereof, vitamin E, a derivative or pharmaceutically acceptable salt thereof and vitamin C, a derivative or pharmaceutically acceptable salt thereof and instructions for use of said composition in the treatment of oxidative liver injury.

14. A kit comprising : individual dosage units of S-adenosylmethionine, a derivative or pharmaceutically acceptable salt thereof, vitamin E, a derivative or pharmaceutically acceptable salt thereof and vitamin C, a derivative or pharmaceutically acceptable salt thereof and instructions and instructions for use of said dosage units in the treatment of oxidative liver injury.

* * * * *